(12) United States Patent
Hershey et al.

(10) Patent No.: US 9,439,629 B2
(45) Date of Patent: Sep. 13, 2016

(54) SPUTUM TRAP

(71) Applicant: AVENT, INC., Alpharetta, GA (US)

(72) Inventors: Adrienne A. Hershey, Cumming, GA (US); Joseph A. Cesa, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 576 days.

(21) Appl. No.: 13/851,598

(22) Filed: Mar. 27, 2013

(65) Prior Publication Data

US 2014/0294698 A1 Oct. 2, 2014

(51) Int. Cl.
   *B01L 3/14* (2006.01)
   *A61B 10/00* (2006.01)
   *B01L 3/00* (2006.01)

(52) U.S. Cl.
   CPC ....... *A61B 10/0051* (2013.01); *A61B 10/0096* (2013.01); *B01L 3/502* (2013.01); *B01L 3/508* (2013.01); *B01L 2200/026* (2013.01); *B01L 2200/082* (2013.01); *B01L 2300/045* (2013.01); *B01L 2300/0822* (2013.01); *B01L 2300/123* (2013.01); *B01L 2400/0481* (2013.01)

(58) Field of Classification Search
   CPC .......... B01L 3/50; B01L 3/502; B01L 3/508; G01N 1/2086; G01N 1/2813; G01N 35/00029; G01N 2035/00138
   USPC .......... 422/547, 548, 501, 549; 436/63, 177, 436/180

IPC .............................................. B01L 3/502,3/508
   See application file for complete search history.

(56) References Cited

U.S. PATENT DOCUMENTS

| | | | |
|---|---|---|---|
| 6,253,807 | B1 | 7/2001 | Jones |
| 6,805,842 | B1 | 10/2004 | Bodner et al. |
| 7,114,403 | B2 | 10/2006 | Wu et al. |
| 7,479,131 | B2 | 1/2009 | Mathias et al. |
| 2004/0007650 | A1* | 1/2004 | Cortelazzo ............ 248/200 |
| 2005/0106753 | A1 | 5/2005 | Wu et al. |
| 2005/0119589 | A1 | 6/2005 | Tung et al. |
| 2009/0226883 | A1* | 9/2009 | Wu et al. .............. 435/4 |
| 2010/0089399 | A1 | 4/2010 | Landis et al. |
| 2010/0281955 | A1 | 11/2010 | Ting et al. |

FOREIGN PATENT DOCUMENTS

WO    WO2011029450 A1    3/2011

* cited by examiner

*Primary Examiner* — Jill Warden
*Assistant Examiner* — Dwayne K Handy
(74) *Attorney, Agent, or Firm* — Dority & Manning, P.A.

(57) ABSTRACT

There is provided a system having a sputum trap or container that is used to transfer a portion of a sample to a sample slide. The container has a body with a top and bottom. The bottom is adapted to accept the sample slide. The bottom also has a one way valve to allow transfer of a portion of the sample to the sample slide upon manipulation of the body by a user. In certain embodiments, the body may be manipulated by squeezing it or by pushing down on the top. The bottom of the container is adapted to receive the sample slide so that the sample can be transferred to it.

6 Claims, 2 Drawing Sheets

SPUTUM TRAP

The present disclosure relates generally to the field of medicine and more particularly relates to sample collection and delivery to a test device.

When a patient is admitted to a hospital, or a specific unit of the hospital, e.g.; the ICU (intensive care unit), they are often tested for the presence of infection causing microorganisms in their system through blood, urine, skin, and sputum. Depending on hospital protocol this screening test is completed upon admission to the various areas of the hospital or upon clinical signs of infection including fever, increased white blood cell count, discolored sputum, purulent sputum, decreased oxygenation, hazy chest X-ray, etc.

Currently, the sputum samples are obtained via bronchoscopy, non-bronchoscopic broncheoaveolar lavage (BAL), closed suction catheter, open suction catheter, or expectorated sample. The sample is then retained in a separate sputum trap container that is connected to the sampling device through flexible tubing connections or other means. Current sputum traps are prone to leakage or spillage, causing concern to the medical personnel involved since the exact microorganisms present are unknown. The disconnection of tubing from current sputum traps is also a source for leakage.

The sample in the sputum trap is transported to the clinical microbiology laboratory for microbial testing and analysis. The sputum trap is commonly transported in a pneumatic system from the ICU to the lab. A problem that sometimes arises is that the sample can spill or leak in the pneumatic tubing as it is being transported. This can contaminate the pneumatic system, putting the integrity of other samples transported at risk and requiring a re-sampling of the patient, with its concomitant risks.

Once a sample is obtained it is usually subjected to a number of rounds of microbiological and other tests. The first round of microbial data that a physician receives is called a gram stain. A gram stain identifies if a bacterial organism is in either the gram negative (GN) or gram positive (GP) class and the morphology of the bacteria (i.e. cocci, rod, etc.) This allows the clinician to remove antibiotic(s) that affect the class of organisms with which the patient is not infected. A gram stain test takes approximately 1 hour to perform, but with transportation time of the sample and the typical lab testing back-log, our results show that most ICU clinicians receive the gram stain results in 12-24 hours. During this time a patient is placed on the 3-5 broad spectrum antibiotics mentioned above until the clinician reviews the gram stain results and removes 1-3 unnecessary broad spectrum antibiotics.

The second round of microbial data that a physician receives is called a microbial specificity. These results are obtained in 24-48 hours and require culturing of the organisms on an agar plate. Microbial specificity identifies the exact organism(s) that are causing the infection and the concentration of that organism(s) in a quantitative or semi-quantitative fashion. These results allow the clinician to change the broad spectrum antibiotics to antibiotics targeted for the specific organism that is causing the infection. The clinician may also wait to change antibiotics if the patient is improving or until further results are obtained.

The third round of microbial data that a physician received is call antibiotic sensitivities. These results are obtained in 48-72 hours and require testing the cultured sample against known antibiotics to determine the resistance pattern of the organism. Once it is know what antibiotics the organism is sensitive to or will kill the organism(s), the clinician can change to one targeted antibiotic to treat the infection.

The current method of taking a sample from a sputum trap involves removing the cap from the trap, inserting a pipette and manually removing a portion of the sample. This takes time and risks exposure of the technician to the microbes in the sample, especially if it needs to be done repeatedly as outlined above. If the sample has been transported, especially in a pneumatic system, the outside of the container (trap) may have sample liquid spilled on it, again possibly exposing the technician to the microbes in the sample. The sample is very precious for the several tests due to its low volume. Any spills of the sample may be cause for resampling, additional procedures and increase risk to the patient.

Thus, there remains a need in the art for a sample container that does not easily spill its contents. There is a need for a sample container that obviates the need for pipetting, with its inherent risks to the user. It would also be helpful if the container interconnected with a sample slide that could be examined by a technician, e.g. under a microscope, or that could be used in an automated system of microbial identification. The suitable system will improve the time it takes for the physician to receive microbial results and allow the physician to make better antibiotic prescription choices to decrease antibiotic resistance, decrease toxicity for the patient, potentially improving patient outcome, saving time in beginning proper treatment and saving money currently used on inappropriate medication.

SUMMARY

In response to the difficulties and problems discussed herein, the present disclosure provides a system having sputum trap or container that is used with a sample slide. The container can direct a portion of the sample to the sample slide. Such slides are commonly used in automated gram stainers such as the AGS-1000 automated gram stainer available from the GG&B Company, 3411 McNiel Ave., Suite 302, Wichita Falls, Tex. 76308. Automated gram strainers can be used to provide an indication of gram negative (GN) or gram positive (GP) infection (or both) within 30 minutes.

The container has a body with a top and bottom attached and the bottom has a one way valve to deliver a portion of a sample to a sample slide upon manipulation of the container by a user. The bottom is also adapted to accept the sample slide. The container for holding the sample and delivering it to the slide may have flexible or deformable sides so that a user may manipulate the container by squeezing the container to force a small amount of the sample out of the container through a one-way valve and desirably onto the slide. Alternatively the container may have relatively rigid or inflexible walls and yet allow the sample to be expelled by compressing the container downwardly to force an amount or portion of sample out of the container.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which.

DETAILED TECHNICAL DESCRIPTION

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment, may be used on another embodiment to yield a still further embodiment. Thus, it is intended that the present disclosure covers such modifications and variations as come within the scope of the appended claims and their equivalents.

Figure 1A:
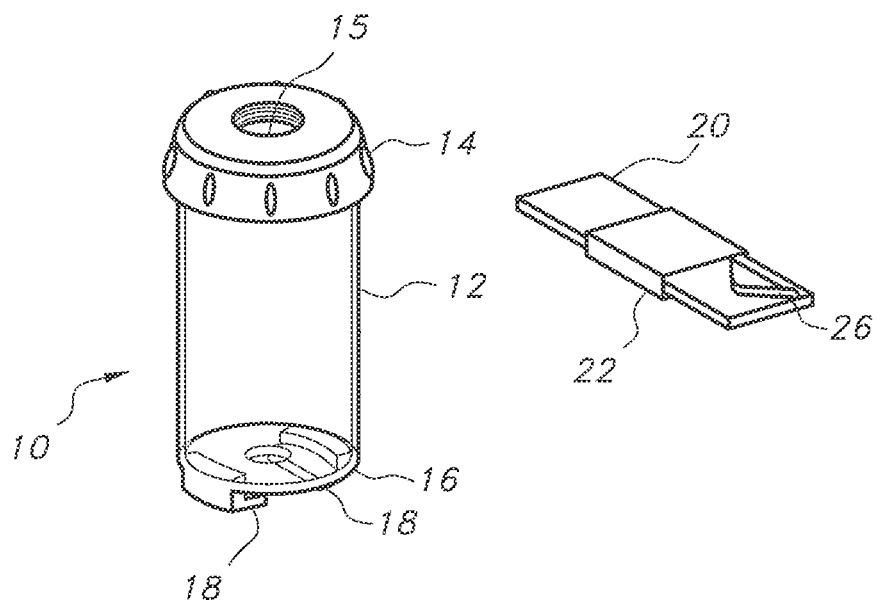
FIG. 1A is a perspective view of one embodiment of a container having flexible walls and that may be squeezed to force a portion of a sample out of the container. There is also shown a closed sample slide separate from the container.

This disclosure describes a system using a sputum trap or container that is used to transfer a portion of a sample to a sample slide. In one embodiment of the trap 10 as shown in FIG. 1A, the trap 10 has a desirably round body 12. The body is preferably clear so that the level of material inside can be seen.

The trap 10 has a top 14 that is desirably removable. The top 14 may be secured to the body 12 by conventional means such as by screwing the together, by a snap connection or other means known to those skilled in the art. The top 14 also desirably has an access port 15 that may be used to add reagents, e.g. a running buffer, or other materials to the sample. The access port 15 desirably allows addition to the trap 10 but does not allow sample material to exit the trap 10 if the trap 10 is overturned.

The trap 10 has a bottom 16 that is desirably adapted to mate with a sample slide 20. The bottom 16 also has a one way or "check" valve that will allow sample to flow out of the trap 10, desirably downwardly, but not allow liquid to enter the trap 10. As can be seen in FIGS. 1A and 2A, the bottom 16 has two tabs 18 that can accommodate the slide 20 and hold the slide in place under the bottom. The bottom also may have a stop (not visible) to limit the insertion of the slide 20 into the tabs 18. The stop ensures that the slide 20 is inserted into the tabs 18 a sufficient distance to position the sample deposition area 24 of the slide 20 directly below the check valve. In this manner the slide 20 is registered to the trap 10 when the slide 20 is inserted into the tabs 18 so that the sample is place in the correct location on the slide 20. Alternatively, the slide 20 may have one or more detents on a side or surface that contacts a corresponding structural feature on one or both tabs 18 to stop the movement of the slide 20 at the proper location below the trap 10. An illustrative example of a detent and corresponding feature combination is a notch in the side of the sample slide and an element on the tab that can protrude into the notch and recess within the tab.

The slide 20 may have a movable cover 22 that shields the sample deposition area 24 of the slide 20 in a first position so that airborne particles or other extraneous materials are prevented from landing in the sample deposition area 24 and potentially contaminating the sample when the slide 20 is not mated to the trap 10. The cover 22 desirably moves out of the way of sample deposition from the trap 10 onto the slide 20 to a second position when the slide 20 is mated to the trap 10 upon insertion of the slide 20 into the tabs 18, as can be seen in the figures. As the slide 20 is mated to the bottom of the trap 10 using the tabs 18, the cover 22 contacts the trap 10 and is pushed over the slide 20 as the sample deposition area 24 moves under the trap 10. The cover 22 can also be made to position the sample deposition area 24 under the one way valve in the absence of a registering stop or mated detent arrangement between the tabs 18 of the container and the slide 20. In ways similar to those previously described between the tabs and slide, stop or detent arrangements between the cover 22 and the slide 20 can limit the insertion of the slide with respect to tabs 18 to properly position the sample deposition area 24 of slide 20 under the one way valve of trap 10.

Self-movement of cover 22 over slide 20 during insertion of the slide into tabs 18 allows the sample to transfer from the trap 10 to the sample deposition area 24 of the slide 20 with minimal to no ambient contamination. The slide 20 may have a means of moving the cover 22 back over the sample deposition area 24 when the slide 20 is withdrawn from the tabs 18. Such means may include a spring 26 molded into the slide 20 as shown. Alternatively, a user can manually move the slide cover 22 over the sample deposition area 24. Other common means known to those skilled in the art may also be used.

Figure 1B:
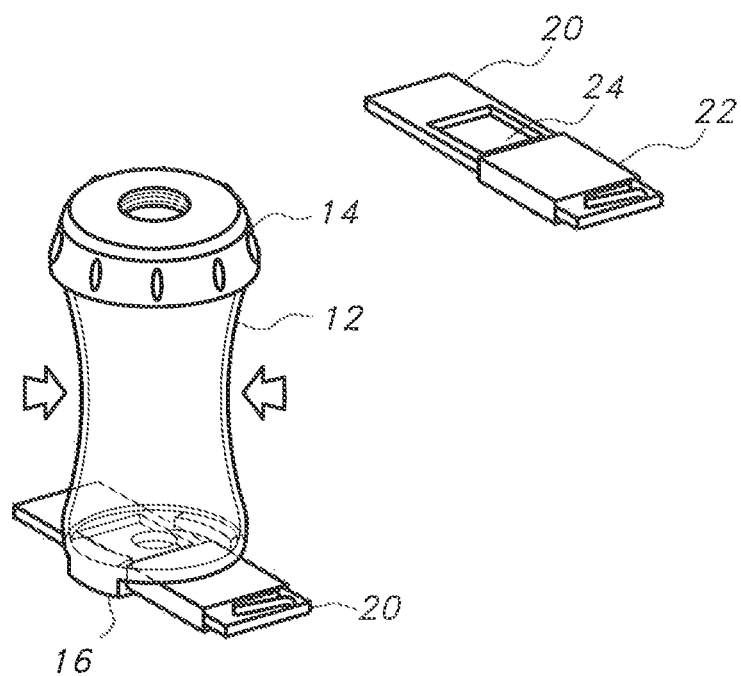
FIG. 1B shows the container and slide of FIG. 1A after they are combined. An enlarged view of the open slide is included.

Once the slide 20 is inserted into the tabs 18 and mated to the trap 10, the sample may be moved from the trap 10 to the slide 20 by a variety of means. FIG. 1B shows the sides of the trap 10 being moved inwardly (indicated by arrows on either side), desirably by means of a user's hands. If the body 12 of the trap 10 is sufficiently flexible, squeezing the body 12 will result in a portion of the sample being forced out of the trap 10 onto the slide 20.

Figure 2B:
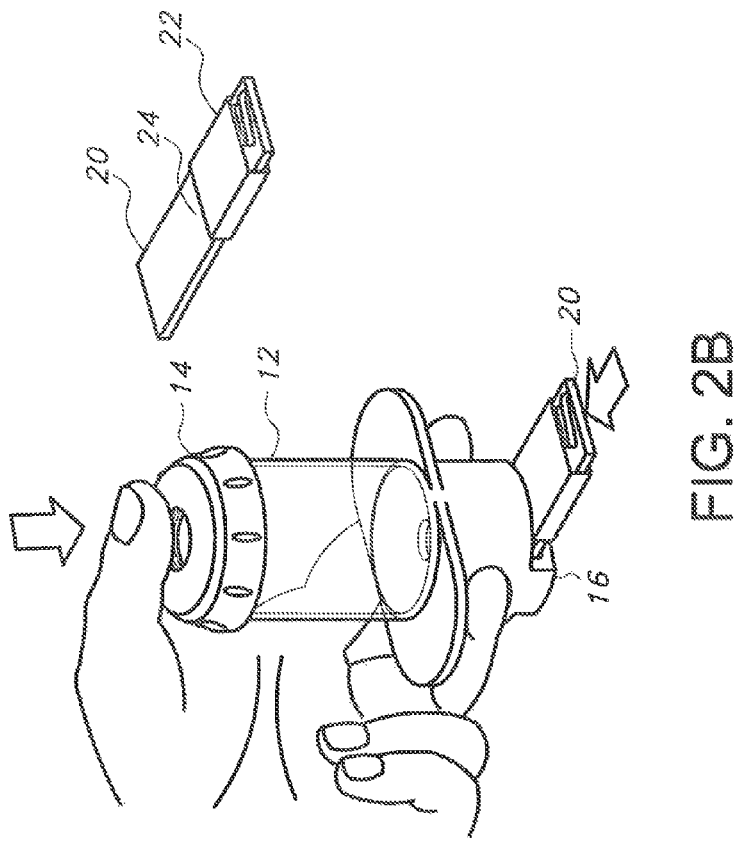
FIG. 2B shows the container and slide of FIG. 2A after they are combined. An enlarged view of the open slide is included.
Figure 2A:
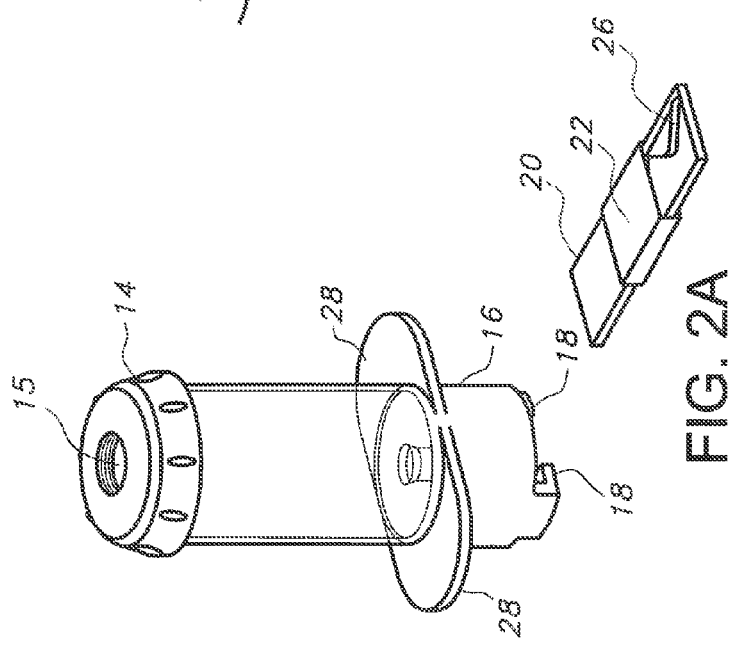
FIG. 2A is a perspective view of another embodiment of a container. This embodiment has rigid walls and the body of the container moves downwardly to force a portion of the sample out. There is also shown a closed sample slide separate from the container.

FIG. 2B shows an embodiment in which the body 12 is more rigid than in the embodiment of FIG. 1B. The body 12 is supported by a spring (not visible) and sealed to the bottom with an O-ring (not visible). This allows the body 12 to move downwardly into the bottom 16 when the body is pushed down (indicated by arrow above trap), desirably by the hand of a user. In this embodiment it is also desirable that the bottom 16 has wings 28 on either side to provide a gripping surface for the fingers of the user.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A system for holding and transferring a sample, comprising:
   a sample slide;
   a flexible container configured to be placed atop said sample slide, said flexible container comprising a body with an access opening, a top, and a bottom configured to secure said sample slide thereto, said bottom of said container comprising one more tabs configured to receive said sample slide and an opening aligned with a one way valve, the one way value configured to transfer a portion of said sample from said container to said sample slide upon manipulation of said body by a user;

said sample slide comprising a movable cover in a first position that shields a sample deposition area of the slide so that airborne particles or other extraneous materials are prevented from entering the sample deposition area, when said slide is not mated to said container;

said cover having a second position away from said sample deposition area when said slide is mated to said container.

2. The system of claim 1, wherein said manipulation of said body is by squeezing.

3. The system of claim 1, wherein said manipulation of said body is by pushing downwardly on it.

4. The system of claim 1, wherein the access opening comprises an access port in the top of said container.

5. The system of claim 1, wherein said sample slide comprises a spring configured to force the cover over the sample deposition area when the sample slide is withdrawn from the tabs.

6. The system of claim 5, wherein the spring is molded into said sample slide.

* * * * *